United States Patent [19]

Geibel et al.

[11] Patent Number: 4,743,686

[45] Date of Patent: May 10, 1988

[54] PROCESS FOR THE ISOMERIZATION OF ASOCAINOL

[75] Inventors: Wolfram Geibel, Emmendingen; Wolfgang Herrmann, Merzhausen, both of Fed. Rep. of Germany

[73] Assignee: Godecke Akt., Berlin, Fed. Rep. of Germany

[21] Appl. No.: 931,118

[22] Filed: Nov. 17, 1986

[30] Foreign Application Priority Data

Nov. 28, 1985 [DE] Fed. Rep. of Germany ....... 3541994

[51] Int. Cl.⁴ ........................................... C07D 313/00
[52] U.S. Cl. ................................................... 540/479
[58] Field of Search ......................................... 540/479

[56] References Cited

U.S. PATENT DOCUMENTS 4,415,495 11/1983 Satzinger et al. .................. 540/479
4,649,196 5/1987 Herrmann et al. ................. 540/479

Primary Examiner—Glennon H. Hollrah
Assistant Examiner—D. B. Springer
Attorney, Agent, or Firm—Elizabeth M. Anderson

[57] ABSTRACT

A new catalytic process for the isomerization of asocainol isomers at the 6-position which provides an inexpensive, rapid, and simple method for large scale production of the (R,R) isomer of (R,S) asocainol is asocainol. The (R,R) isomer of (R,S) asocainol is treated with small amounts of a salt and an oxidizing agent at an elevated temperature. The compounds and their pharmaceutically acceptable salts are useful as potent antiarrhythmic agents and local anesthetics.

7 Claims, No Drawings

PROCESS FOR THE ISOMERIZATION OF ASOCAINOL

BACKGROUND OF THE INVENTION (+)-Asocainol or (+)-2,12-dimethoxy-1-hydroxy-7-methyl-6-phenethyl-5,6,8,9-tetrahydro-7H-dibenz(d,-f)azonine or R,R-asocainol is a pharmaceutically active compound described in German Pat. No. 30 07 710. The compound is especially useful as a local anaesthetic and an antiarrhythmic.

In the case of the synthesis of (+)-asocainol according to German Pat. No. 30 07 710, from natural thebaine (see Merck Index, 10th edition, 1983, No. 9097), the hydrochloride is obtained in a yield of 21% of theory. Besides the desired (+)-asocainol with the R,R-configuration, there is formed, in the extremely unfavorable weight ratio of 1:3.25, the ineffective and therefore useless diastereomer with the R,S-configuration. All attempts to shift this unfavorable isomer ratio by alteration of the synthesis parameters, for example by the use of different solvents and variation of the temperature, amount ratio or of the concentration in favor of an increase in yield of the desired isomer remained unsuccessful.

In German Pat. No. 34 19 099, (−)-asocainol (the S,S-isomer) is described as obtainable from the ineffective R,S-isomer by thermal isomerization; it also displays an antiarrhythmic effect. In the case of the synthetic formation of the racemate (R,R; S,S) of equal parts of asocainol in the R,R- and S,S-form, there was a surprising pharmacological finding; instead of the expected additive action, there was a stronger synergistic antiarrhythmic effect by means of which there was considerably improved effectiveness in comparison with (+)-asocainol.

In the case of the thermal rearrangement described in the German Pat. No. 34 19 099 at temperatures of from 130° to 200° C. in the melt or in high boiling point solvents, there is formed, in equilibrium with the starting material, in about 40% yield, the S,S-enantiomer which can be separated by fractional crystallization, for example, as the hydrochloride. By recycling the unreacted R,S-isomer, practically all of the R,S-isomer can be converted into the S,S-form and thus, besides about 17 to 20% of (+)-asocainol (R,R), there can also be obtained about 45 to 50% (−)-asocainol (S,S).

Since, however, as stated above, the greatest action is not obtained with the isomers but with the racemate, this means an undesired excess of S,S-isomer.

Therefore, the problem is to find a process for the isomerization of asocainol whereby the (+)-asocainol (R,R) can also be obtained in order to be able to prepare the highest possible yields of the racemic (±)-asocainol.

According to the X-ray structural analysis, (+)-asocainol possesses an absolute configuration according to the following formula:

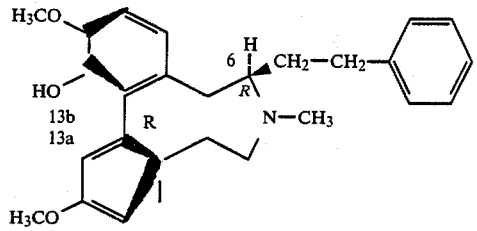

Theoretically, as described in German Pat. No. 34 19 099, asocainol can occur in four different forms which are due to 1. the asymmetric carbon atom in the 6-position and
2. the biphenyl asymmetry at the 13a–13b bond.

The biphenyl asymmetry is brought about because the two phenyl rings do not lie in one plane but rather are arranged almost vertically to one another. Consequently, the following configurations are conceivable: (R,R), (S,S), (R,S), and (S,R). The pair (R,R) and (S,S), as well as the pair (R,S) and (S,R), are enantiomers which theoretically can each form a racemate. Since, in their structure, enantiomers behave like image and mirror image, they are the same in all physical properties apart from the sign of the rotation of polarized light.

Because of the presence of two chiral centers, in the case of asocainol, besides the optical isomerism, there also occurs diastereomerism. Diastereomers are characterized by the fact that they do not have an image-mirror image relationship to one another.

Thus, the pair (R,R) and (S,S) is diastereomeric to the pair (S,R) and (R,S). In the same way, the racemate (R,R-S,S) is a diastereomer of the racemate (S,R-R,S). The configuration first mentioned in the case of the pairs refers, in each case, to the biphenyl asymmetry and the second to the asymmetric carbon atom in the 6-position. (S,R) means S-configuration with regard to the biphenyl asymmetry and R-configuration on C6.

In Scheme II below there are the four possible configurations and their racemates. In addition, in each case the optical rotation is shown.

←——— enantiomers ———→

II.

-continued

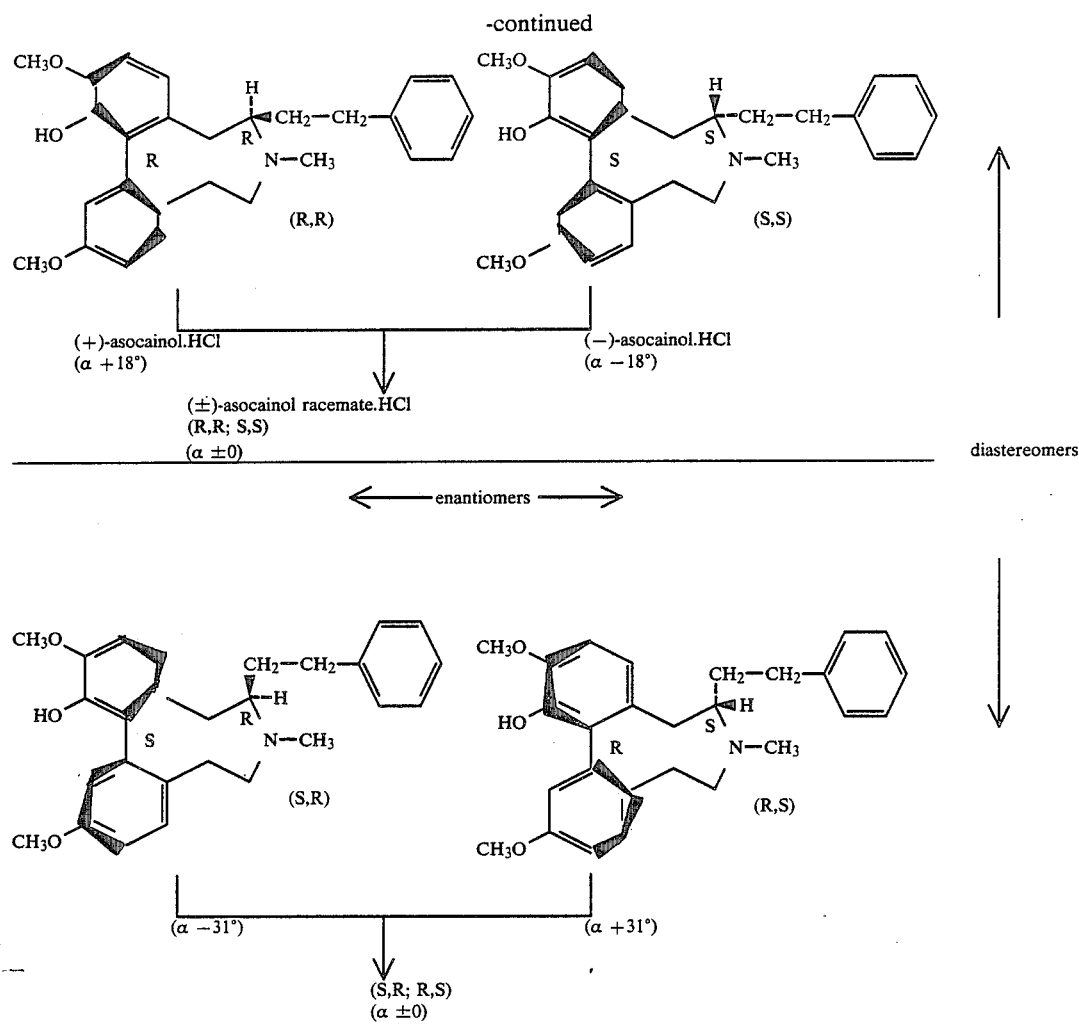

Starting from the R,S-isomers obtained in excess in comparison with the R,R-isomers or from the S,S-isomers obtainable therefrom, various ways were theoretically conceivable for an isomerization for obtaining additional R,R-isomers or the desired racemate:

1. racemization of the R,S-compound to the diastereomeric (S,R; R,S) racemate and subsequent thermal rearrangement of this racemate into racemic asocainol according to German Pat. No. 34 19 099;
2. inversion of the R,S-compound to the S,R-compound and thermal rearrangement of this compound to (+)-asocainol according to German Pat. No. 34 19 099;
3. change of the configuration on the optically-active C6 atom of the R,S-compound from the S- to the R-configuration, (+)-asocainol thereby being formed;
4. simultaneous change of the configuration on the optically-active C6 atom of the R,S-compound from the S- to the R-configuration, (+)-asocainol thereby being formed, and rearrangement of the biphenyl system of the R,S-compound from the R- to the S-configuration to give (−)-asocainol, with the direct formation of the racemic asocainol; both reactions must proceed with the same velocity.

The essential step in the case of all four routes is the change in the configuration of the optically-active C6 atom which, apart from carbon and hydrogen, carries a tertiary amine as the fourth substituent.

Routes 1 and 2 cannot be used because R,S-asocainol could not be racemized with the formation of S,R-asocainol nor could it be isomerized.

SUMMARY

The present invention is an improved process for the isomerization of asocainol isomers at the 6-position which provides greatly improved yields.

A process which comprises:
(a) dissolving asocainol isomers in an organic or organic acid, optionally with a polar solvent,
(b) adding a catalytic amount of a salt and an oxidation agent and/or a salt with an oxidising activity to, the solution
(c) heating the above solution to between 60° and 118° C. to give partial isomerization.

DETAILED DESCRIPTION

Surprisingly, it was found that the R,S-compound in the form of its hydrochloride rearranges in an aqueous solution when heated in a pressure vessel to a temperature above 100° C. partly into R,R- and S,S-asocainol, corresponding to the route indicated in 4 above. The total yield is 50 to 60%. The hydroiodide can also be used, with the same result, for the rearrangement according to route 4. However, a practical use of the rearrangement of R,S-asocainol to racemic asocainol according to route 4 is not obtained since the isomers are always obtained in a ratio other than 1. Attempts to obtain equal amounts of (+)- and (−)-asocainol by alteration of the reaction conditions were unsuccessful. Because of the unequal amount ratios, the isolation of racemic asocainol, i.e. its optical purification, was extremely difficult and laborious and involved large losses of yield.

The solution of the technical problem was, finally, found according to route 3, which is described hereinafter in more detail.

According to present experience with the hydrochloride of the R,S-form, it was to have been expected that, in the case of the use of organic acids, a similar rearrangement would take place. However, it was found not only with trifluoroacetic acid but also with acetic acid, an inversion only on the optically-active C6 atom, i.e. a rearrangement of the R,S-form into the R,R-form, without the configuration of the biphenyl system thereby being influenced.

This rearrangement was observed at temperatures of about 100° C. As solvents, water and/or ethanol can be used, as well as concentrated and aqueous acetic acid.

The extent of the rearrangement is, under these conditions, at most 20% of (+)-asocainol. In spite of a change of the experimental parameters, such as amount of acid, concentration, solvent and temperature, the yield of (+)-asocainol could not be increased, and therefor was not economically satisfactory.

Surprisingly, it was found that, in the case of this reaction with organic acids, the proportion of (+)-asocainol in the reaction mixture could be drastically increased by the addition of salts and oxidation agents. In equilibrium, there was obtained about 55 to 65% of (+)-asocainol and 35 to 45% of R,S-asocainol. This result corresponds to the equilibrium estimated from the enthalpy values and the maximum achievable proportions of both substances. For the achievement of the equilibrium, both substances, salt and oxidation agent, are absolutely necessary, each one alone having no or only a little influence.

The reaction can also be carried out in aqueous mineral acids.

The present invention is a process for the isomerization of asocainol isomers in the 6-position, wherein the isomers are treated at an elevated temperature in a polar solvent containing an inorganic or organic acid with at leat catalytic amounts of a salt and of an oxidation agent and/or with a salt with oxidizing activity.

The reaction according to the present invention has a wide scope of variation with regard to the reaction parameters influencing it. In the following, this scope of variation is described in more detail:

Solvent/acid

Appropriate solvents include aqueous solutions of either inorganic or organic acids, as well as mixtures thereof, optionally with the addition of 10 to 20% by volume of polar organic solvents. For example, hydrochloric acid, sulphuric acid, phosphoric acid and boric acid as preferred inorganic acids. These acids are used in concentrations of from 1 to 5 mol/l. In the case of strong acids, the concentration is preferably 2 mol/l and in the case of weak acids is 5 mol/l.

Besides trifluoroacetic acid (diluted with ethanol), as organic acid, acetic acid can also be used as solvent. Acetic acid can be used not only in an anhydrous state but also as an aqueous solution. The proportion of water can be varied from about 0 to 90% but the preferred proportion is from about 50 to 60% acetic acid. It is assumed that other polar solvents, such as lower alcohols containing up to ten carbon atoms, ketones containing up to ten carbon atoms, for example acetone, ethers, such as diethyl ether, dioxan and tetrahydrofuran, dimethylformamide and dimethyl sulphoxide can be used for the reaction. Instead of trifluoroacetic acid or acetic acid, there can also be used other strong or average strong organic acids. For example, formic acid, hydroxyacetic acid, propionic acid, malonic acid, benzoic acid, oxalic acid, citric acid, tartaric acid, and lactic acid, without thereby limiting the choice. The acids can be used as 10 to 60% by weight solutions and preferably as 40 to 60% by weight solutions. This corresponds to about 1 to 20 and preferably 5 to 15 equivalents of asocainol.

Concentrations

The concentration of asocainol in the solution (≦20%) is not decisive for the result. For practical reasons of carrying out the reaction, also with regard to carrying out on a large scale, it is preferred to use concentrations of from 10 to 20%.

Temperature

Reasonable reaction velocities are first achieved above a reaction temperature of 60° C. Between 60° C. and the reflux temperature (118° C. in concentrated acetic acid), any temperature can be selected. A temperature of about 75° to 85° C. is preferred as an optimal between reaction velocity and avoidance of side reactions.

Salts

A variety of salts can be used for the reaction provided that they are not completely insoluble in the solvent, for example, alkali metal and alkaline earth metal halides, sulphates and acetates, ammonium halides and acetate, as well as transition metal salts, for example ferrous chloride, ferric chloride, cuprous chloride, cupric chloride, copper sulphate, cuprous acetate, zinc chloride, nickel chloride, nickel acetylacetonate, vanadium (III) acetylacetonate and ferric acetylacetonate.

Preferred are sodium chloride, sodium bromide, lithium chloride, lithium bromide, potassium chloride and potassium bromide.

The amount of salt used is from about 10 to 400 mol % and preferably from about 30 to 80 mol %, referred to the asocainol. At concentrations below 10 mol %, the reaction velocity is clearly slowed down (reaction time is three times as long) and above 400 mol % the amounts of salt no longer dissolve completely and, in some cases, give rise to problems due to the formation of two phases as a result of the so-called "salt effect".

Oxidation agents

It is assumed that the oxidation agent brings about an activation at the C6-position due to a reversible redox process on the $C_6$-atom or on the neighboring nitrogen atom.

Therefore, catalytic amounts (1 to 3 mol %) of oxidation agent should suffice for the adjustment of the equilibrium. In order to compensate for unavoidable oxidative side reactions and to make possible a sufficient reaction velocity, it is, however, advantageous to employ larger amounts from about 10 to 50 mol %.

The reaction takes place surprisingly easily with oxidation agents of average strength, whereas with weak oxidation agents, the reaction takes place too slowly and the equilibrium conditions are not achieved. On the other hand, strong oxidation agents, due to over oxidation, lead to high losses of substance and are thus unsuitable as catalysts.

Air, hydrogen peroxide and per acids have been found to be ideal oxidation agents, none of which displayed the described disadvantages. In particular, air and hydrogen peroxide are the oxidation agents of choice. The oxidation agents air and hydrogen peroxide are already effective in catalytic amounts of from 3 mol %. Because of the rapid decomposition of hydrogen peroxide, for the completion of the reaction, about 20 to 30 mol % are necessary. Stoichiometric amounts of both oxidation agents are disadvantageous since substance losses due to oxidative side reactions hereby occur.

Salts which are simultaneously also oxidation agents, for example cupric chloride, cupric acetate, ferric chloride and the like, can be used simultaneously as salt and oxidation agent. Thus, for example, with 50 mol % cupric chloride, yields of 40 to 50% (+)-asocainol have been achieved in the reaction mixture. However, the use thereof can give rise to ecological problems. Their ability, in some cases, to participate in further reactions of other kinds, for example chlorination by cupric chloride or ferric chloride, further limits their use.

The oxidation agents investigated can be classified on the basis of their redox potentials. Up to a redox potential of about 1 volt, the oxidation agents give no or only slight losses of substance due to overoxidation. It is assumed that individual oxidation agents with a higher redox potential, for example sodium iodate and manganese dioxide, can also be used.

Under these reaction conditions, there can be converted not only the R,S-isomer into the R,R-isomer but also the other isomers, as well as the racemates. The relationships of the isomers and racemates which can be converted into one another are set out in the following:

R,R⇌R,S

S,R⇌S,S

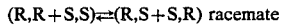

(R,R+S,S)⇌(R,S+S,R) racemate

Together with the thermal isomerization described German Pat. No. 34 10 099, by means of which R,S can be converted into S,S and S,R into R,R, every desired isomer can now be prepared.

Due to the fact that the by-product previously only of limited usefulness by conversion into (−)-asocainol, i.e. the R,S-isomer, can now also be converted into (+)-asocainol, the whole of the substance material introduced by expensive thebaine can now be used for the preparation of the racemate (±)-asocainol (R,R+S,S). Besides the reduction of the preparation costs thereby achieved, this process also represents a simple, rapid method which can be carried out on a large scale in order to utilize all isomers obtained in the case of total syntheses for conversion into (±)-asocainol.

The following Examples serve to illustrate the present invention and are not intended to limit the scope in any way.

EXAMPLE 1

Preparation of
(+)-6,7,8,9-tetrahydro-2,12-dimethoxy-7-methyl-6(e')-phenethyl-5H-dibenz(d,f)azonin-1-ol hydrochloride (R,R-asocainol hydrochloride)

One kg (2.4 moles) R,S-asocainol is dissolved in 4.3 liters 54% acetic acid in a 10 liter reaction vessel. After the addition of 500 g (8.5 mole) sodium chloride, the mixture is heated to reflux and compressed air is passed in a gentle current over or into the solution. The reaction is finished after 1.5 hours. Subsequently, the reaction mixture is evaporated to dryness in a vacuum. The composition of the residue is determined by HPLC. The content of R,R-asocainol amounts to 55 to 60% and that of R,S-asocainol to 40 to 45%.

Purification

The residue obtained is taken up in 5 liters of water and 5 liters of methylene chloride, adjusted to a pH of about 8 to 9 with concentrated aqueous ammonia solution and the phases are separated. The aqueous phase is again stirred up with a total of 4 liters of methylene chloride. The combined organic phases are washed neutral with water and subsequently dried over a mixture of anhydrous sodium sulphate and 100 g fuller's earth. After filtration, 69.8 g gaseous hydrogen chloride (80% of theory) in 400 ml isopropanol are added to the filtrate. After the addition of another 4 liters of isopropanol, all the methylene chloride is removed at 50° C. under a low vacuum. The precipitation of R,R-asocainol hydrochloride is completed by stirring for an hour in an ice bath and the crystallizate is filtered off, washed with isopropanol and dried at 70° to 90° C. in a circulation drying cabinet.

There was obtained 512 g (+)-6,7,8,9-tetrahydro-2,12-dimethoxy-7-methyl-6(e')-phenethyl-5H-dibenz(d,f)-azonin-1-ol hydrochloride (R,R-asocainol hydrochloride); 47.2% of theory; mp 230° C.; $[\alpha]_D = +17.6°$ (C=1/water); HPLC content 99%.

The base is liberated from the mother liquor of the above-described hydrochloride precipitation by the addition of ammonia solution. It is isolated and reprecipitated from methylene chloride-isopropanol. Recovered is 413 g of R,S-asocainol contaminated by R,R-asocainol (41% of theory); mp 135° C.; HPLC content: 93.5% R,S-asocainol and 5.4% R,R-asocainol.

The mixture can be used again for the rearrangement without further purification.

EXAMPLE 2

Preparation of
(+)-6,7,8,9-tetrahydro-2,12-dimethoxy-7-methyl-6(e')-phenethyl-5H-dibenz(d,f)azonin-1-ol hydrochloride (R,R-asocainol hydrochloride)

Twenty grams (0.048 moles) R,S-asocainol are dissolved in 100 ml 60% acetic acid, mixed with 2 g (0.034 moles) sodium chloride and heated to 80° C. Air is passed over the solution for 1.5 hours while stirring. After completion of the reaction, the reaction mixture is completely evaporated to dryness in a vacuum. According to HPLC, the residue consists of 53% R,R-asocainol and 47% R,S-asocainol. A process analogous to Example 1 gives 9.5 g R,R-asocainol hydrochloride (44% of theory); mp 236.2° C.; HPLC content 95%.

The product is purified by precipitation from methylene chloride-isopropanol.

EXAMPLE 3

Twenty grams (0.048 moles) R,S-asocainol are heated to 80° C. under nitrogen in 100 ml 60% acetic acid with 2 g (0.034 moles) sodium chloride. Over the course of one hour, 469 g (0.0138 moles) hydrogen peroxide in 2.5 ml water are gradually added thereto. The reaction mixture is allowed to react further for half an hour at 80° C. A process analogous to Example 1 gives, according to HPLC, a residue consisting of 52% R,R-asocainol and 48% R,S-asocainol.

EXAMPLE 4

Ten grams (0.024 moles) R,S-asocainol and 1 g (0.017 moles) sodium chloride are mixed with 2 ml 35% hydrochloric acid (0.023 moles), dissolved in 50 ml 80% acetic acid and heated to 80° C. After the addition of 40.6 mg (0.0012 moles) hydrogen peroxide in 0.36 ml water, the reaction mixture is stirred for one hour and a further 40 mg hydrogen peroxide in 0.36 ml water are added thereto. The reaction is allowed to continue for two hours at 80° C. and the reaction proceeds as in Example 1 to give 4 g R,R-asocainol hydrochloride (37% of theory); $[\alpha]_D = +17.6°$ (C=1.02/water).

The product is obtained pure by reprecipitation from methylene chloride/isopropanol.

Preparation of
(+)-6,7,8,9-tetrahydro-2,12-dimethoxy-7-methyl-(6a')-phenethyl-5H-dibenz(d,f)azonin-1-ol (R,S+S,R racemate)

EXAMPLE 5

Ten grams (0.024 moles) R,S-asocainol and 1 g (0.017 moles) sodium chloride are dissolved in 50 ml. 3M aqueous phosphoric acid and heated to 90° C. After the addition of 50 mg (0.0014 moles) hydrogen peroxide (1 ml of a 5% solution), the reaction mixture is stirred for one hour and a further 50 mg hydrogen peroxide (1 ml of a 5% solution) are added thereto. After a post-reaction for one hour at 90° C., the reaction proceeds as in Example 1. According to HPLC, the residue contains 42% R,S-asocainol and 51.4% R,S-asocainol. The R,R-asocainol hydrochloride is obtained pure by reprecipitation from methylene chloride-isopropanol.

EXAMPLE 6

Ten grams (0.024 moles) R,S-asocainol and 1 g (0.017 moles) sodium chloride are dissolved in 50 ml 80% acetic acid, mixed with 3.09 g (0.05 moles) boric acid and heated to 80° C. After the addition of 50 mg (0.0014 moles) hydrogen peroxide (1 ml of a 5% solution), the reaction mixture is stirred for 30 minutes and a further 50 mg hydrogen peroxide (1 ml of a 5% solution) added thereto. The reaction is allowed to continue for 30 minutes at 80° C. and then the reaction proceeds as in Example 1. According to HPLC, the residue contains 57% R,R-asocainol and 39% R,S-asocainol.

EXAMPLE 7

Ten and one-half grams (0.025 moles) racemic R,R-+S,S-asocainol are dissolved in 50 ml 60% acetic acid, mixed with 1 g (0.017 moles) sodium chloride and heated to reflux. Air is passed into the solution for two hours. When the reaction is finished, the reaction mixture is evaporaed in a vacuum. According to HPLC, the residue obtained contains 62% of starting material and 38% of R,S+S,R-racemate. In a process analogous to Example 1 5.9 g of starting material (52% of theory) as hydrochloride are recovered; mp 213° C.; HPLC composition: 94.5% R,R+S,S-racemate and 5.5% R,S+S,R-racemate.

The base is obtained with concentrated ammonia solution from the mother liquor of the above precipitation and extracted with methylene chloride. The organic phase is washed neutral with water and dried over anhydrous sodium sulphate and fuller's earth. The solution is filtered and subsequently the methylene chloride is removed in a low vacuum. According to HPLC, the precipitated residue consists of about 5% R,R+S,S-racemate and about 94% R,S+S,R-racemate. Yield about 4 g (38% of theory).

For purification, the base is converted into the hydrochloride and recrystallized from aqueous hydrochloric acid.

We claim:

1. A process for the isomerization of asocainol isomers at the six position which comprises:
    (a) dissolving asocainol isomers in an acid selected from the group consisting of hydrochloric acid, sulphuric acid, phosphoric acid, boric acid, trifluoroacetic acid, and acetic acid, with or without a polar solvent;
    (b) adding a catalytic amount of from 1 to 50 Mol% of a salt selected from the group consisting of lithium chloride, sodium chloride, lithium bromide, sodium bromide, potassium chloride, and potassium bromide and an oxidation agent selected from the group consisting of air, hydrogen peroxide or a peracid or a salt with oxidizing activity selected from the group consisting of a cupric or ferric salt to the solution;
    (c) heating the above solution to between 60° to 118° C. to give isomerization of 55 to 65% of (+)-asocainol and 35 to 45% of R,S-asocainol.

2. A process according to claim 1, wherein the amount of the salt used is from about 0.1 to about 4.0 mole per mole of asocainol.

3. A process according to claim 1, wherein in the amount of the salt used is from about 0.3 to about 0.8 mole per mole of asocainol.

4. A process according to claim 1, wherein the acid used is in a concentration of from 1 to 20 mole per mole asocainol.

5. A process according to claim 1, wherein the concentration of the oxidation agent is from about 0.01 to about 0.5 per mole per mole of asocainol.

6. A process according to claim 5, wherein the concentration of the oxidation agent is from about 0.03 to about 0.3 per mole per mole of asocainol.

7. The process according to claim 1, wherein in step (c) the temperature is from about 75° C. to 85° C.

* * * * *